US012282123B2

(12) United States Patent
Junnarkar et al.

(10) Patent No.: US 12,282,123 B2
(45) Date of Patent: Apr. 22, 2025

(54) READOUT AND PROCESSING ARRANGEMENT IN A SENSOR SYSTEM

(71) Applicant: Sachin S Junnarkar, Vernon Hills, IL (US)

(72) Inventors: Sachin S Junnarkar, Vernon Hills, IL (US); Pushkar, Samastipur (IN)

(73) Assignee: Sachin S Junnarkar, Vernon Hills, IL (US)

( * ) Notice: Subject to any disclaimer, the term of this patent is extended or adjusted under 35 U.S.C. 154(b) by 191 days.

(21) Appl. No.: 17/658,095

(22) Filed: Apr. 6, 2022

(65) Prior Publication Data

US 2022/0357468 A1 Nov. 10, 2022

Related U.S. Application Data

(60) Provisional application No. 63/184,237, filed on May 5, 2021.

(51) Int. Cl.
*G01T 1/24* (2006.01)
*A61B 6/00* (2006.01)
(Continued)

(52) U.S. Cl.
CPC .............. *G01T 1/175* (2013.01); *A61B 6/037* (2013.01); *A61B 6/56* (2013.01); *G01T 1/243* (2013.01); *G01T 1/247* (2013.01)

(58) Field of Classification Search
CPC .................................. A61B 6/037; A61B 6/56
See application file for complete search history.

(56) References Cited

U.S. PATENT DOCUMENTS 5,629,839 A * 5/1997 Woychik ................. H05K 3/366
439/55
6,621,084 B1 * 9/2003 Wainer .................... G01T 1/244
250/370.01
(Continued)

FOREIGN PATENT DOCUMENTS

KR 10-2019-0138208 A 12/2019

OTHER PUBLICATIONS

Texas Instruments Incorporated ACF2101 datasheet, 17 pages (Year: 2010).*

(Continued)

*Primary Examiner* — David P Porta
*Assistant Examiner* — Shun Lee
(74) *Attorney, Agent, or Firm* — IPHORIZONS PLLC; Narendra Reddy Thappeta (57) ABSTRACT

A sensor system includes a detector substrate, multiple readout substrates and a processing substrate. The detector substrate has a detector mounted thereon. Each of the readout substrates is disposed perpendicular to the detector substrate, and has corresponding readout circuitry mounted thereon. The processing substrate is disposed perpendicular to each of the readout substrates and parallel to the detector substrate, and has one or more processing elements mounted thereon. Electrical connections between component nodes on the detector substrate and corresponding readout substrates are made using connectors or right-angled solder joints created using a solder reflow process. Electrical connections between component nodes on the processing substrate and corresponding readout substrates are also made using connectors or right-angled solder joints created using a solder reflow process. The geometric arrangement of the substrates allows for high density of pixelation on the (Continued)

detector. In an embodiment, the sensor system is a radiation detector system.

13 Claims, 11 Drawing Sheets

(51) Int. Cl.
*A61B 6/03* (2006.01)
*G01T 1/175* (2006.01)

(56) References Cited

U.S. PATENT DOCUMENTS

| | | | |
|---|---|---|---|
| 6,800,942 B1 * | 10/2004 | Kinsman | H01L 25/0657 |
| | | | 257/737 |
| 6,841,784 B2 | 1/2005 | Brahme et al. | |
| 7,170,049 B2 | 1/2007 | Iwanczyk et al. | |
| 7,758,843 B1 | 7/2010 | Bolotnikov et al. | |
| 8,824,635 B2 | 9/2014 | Tkaczyk et al. | |
| 2003/0010924 A1 | 1/2003 | El-Hanany et al. | |
| 2004/0217294 A1 | 11/2004 | Zur | |
| 2012/0193545 A1 * | 8/2012 | Tkaczyk | G01T 1/2928 |
| | | | 250/370.08 |
| 2013/0026380 A1 * | 1/2013 | Tkaczyk | G01T 1/2928 |
| | | | 438/73 |
| 2013/0108019 A1 * | 5/2013 | Tkaczyk | G01T 7/005 |
| | | | 438/73 |
| 2013/0193336 A1 | 8/2013 | Washington et al. | |
| 2013/0284938 A1 * | 10/2013 | Meng | G01T 1/24 |
| | | | 250/370.09 |
| 2016/0148966 A1 | 5/2016 | Lin et al. | |

OTHER PUBLICATIONS

Alicja Michalowska, Studies and development of a readout ASIC for pixelated CdTe detectors for space applications, https://tel.archives-ouvertes.fr/tel-00956027/file/VD2_MICHALOWSKA_ALICJA_10122013.pdf, Mar. 5, 2022, 296 Pages.

W. C. Barber, et al, Energy dispersive CdTe and CdZnTe detectors for spectral clinical CT and NDT applications, https://www.ncbi.nlm.nih.gov/pmc/articles/PMC4415629/, Nov. 18, 2014, 15 Pages.

L.-J. Meng, Energy-Resolved Photon Counting Detector—Design Concept and Considerations, https://indico.cern.ch/event/102998/contributions/17182/attachments/10555/15436/presentation_v3.pdf, 2011, 27 Pages.

SOMATOM go.Top with myExam Companion, https://www.siemens-healthineers.com/en-in/computed-tomography/single-source-ct-scanner/somatom-go-top, Downloaded circa Jul. 28, 2021, 12 Pages.

* cited by examiner

READOUT AND PROCESSING ARRANGEMENT IN A SENSOR SYSTEM

PRIORITY CLAIM

This present patent application is related to and claims the benefit of priority to the provisional US patent application entitled, "Radiation Detector System", Ser. No. 63/184,237, Filed: 5 May 2021, the entire contents of which is incorporated by reference herein in its entirety to the extent not inconsistent with the description herein.

BACKGROUND

Technical Field

Embodiments of the present disclosure relate generally to sensor systems, and more specifically to a readout and processing arrangement in a sensor system.

Related Art

Sensor systems are well known in the art, and refer to systems that contain one or more sensors (transducers), readout circuitry and processing circuitry. The sensors generate sensor output signals indicative of a physical phenomenon. The readout circuitry generally performs one or more of collecting, conversion to another form, signal-conditioning and storage of the sensor output signals, and forwards the collected, converted, conditioned and/or stored sensor output signals as readout output signals. The processing circuitry performs operations on the readout output signals to extract and process information of interest in the readout output signals. An example of a sensor system is a radiation detection system for detecting and processing gamma rays.

A typical sensor system may contain several individual sensors (or sensor portions), and therefore, a readout circuit may need to readout several sensor output signals simultaneously. For example, in a gamma ray radiation detector system noted above, a gamma ray (also known as gamma photon) detector may be formed as a combination of several pixels (or pixelated portions) of a suitable sensor/detector material in an X-Y plane on a sensor substrate, with each pixel capable of generating a corresponding charge representing the intensity of the gamma photons impinging thereupon.

A higher density of pixels on a sensor enables more number of pixel outputs for a given area of the sensor, and therefore higher resolution and greater detail in the information that can be obtained from the sensor by processing circuitry. For example, a high density pixelation of a gamma detector can enable a processing circuitry to generate and analyze a higher-resolution image of the source (e.g., human body) of the gamma photons. However, higher pixel density generally translates to a smaller area/space available for readout of each pixel, thereby making the electrical connections between the sensor and the readout circuitry, and between the readout circuitry and processing circuitry more difficult to achieve.

Several aspects of the present disclosure are directed to a readout and processing arrangement in a sensor system.

BRIEF DESCRIPTION OF THE VIEWS OF DRAWINGS

Example embodiments of the present disclosure will be described with reference to the accompanying drawings briefly described below.

In the drawings, like reference numbers generally indicate identical, functionally similar, and/or structurally similar elements. The drawing in which an element first appears is indicated by the leftmost digit(s) in the corresponding reference number, unless noted otherwise in the description below.

DETAILED DESCRIPTION

1. Overview

A sensor system provided according to an aspect of the present disclosure includes multiple readout substrates disposed perpendicular to a detector substrate. Such a geometrical arrangement allows for high density of pixelation on the detector substrate. The sensor system further includes a processing substrate also disposed perpendicular to each of the readout substrates and parallel to the detector substrate.

According to another aspect, electrical connections between component nodes on the detector substrate and corresponding readout substrates are made using connectors or right-angled solder joints created using a solder reflow process. Electrical connections between component nodes of the processing substrate and corresponding readout substrates are also made using connectors or right-angled solder joints created using the solder reflow process.

A sensor system provided according to yet another aspect of the present disclosure includes multiple readout substrates disposed perpendicular to a detector substrate. Electrical connections between component nodes on the detector substrate and corresponding readout substrates are made by right-angled solder joints created using a solder reflow process. The technique allows for even greater density of pixelation on the detector substrate.

In an embodiment, the sensor system is a radiation detector system.

Several aspects of the present disclosure are described below with reference to examples for illustration. However, one skilled in the relevant art will recognize that the disclosure can be practiced without one or more of the specific details or with other methods, components, materials and so forth. In other instances, well-known structures, materials, or operations are not shown in detail to avoid obscuring the features of the disclosure. Furthermore, the features/aspects described can be practiced in various combinations, though only some of the combinations are described herein for conciseness.

2. Example Environment

Figure 1:
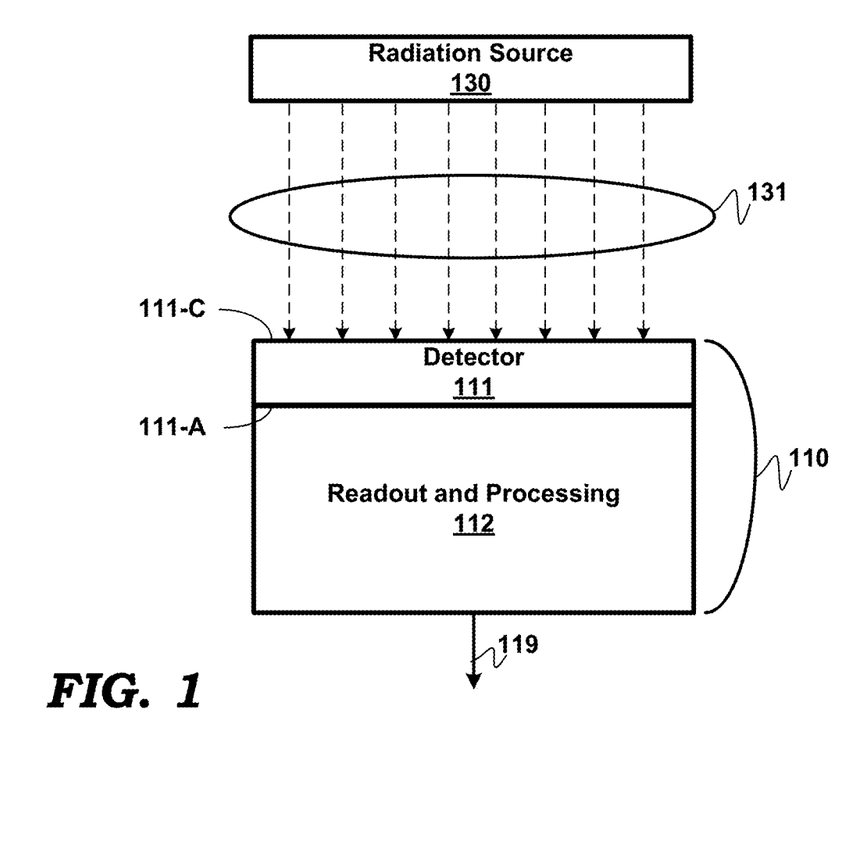
FIG. 1 is a block diagram of an example environment in which several aspects of the present disclosure can be implemented.

FIG. 1 is a block diagram of an example environment in which several aspects of the present disclosure can be implemented. The details and aspects of the present disclosure described below are provided in the context of a radiation detection system in general, and a gamma detector in particular, merely as an illustration. However, aspects of the present disclosure can be applied in any sensor system in general, and therefore include other environments, such as, for example, imaging systems operating on visible light spectrum, data acquisition systems, etc.

FIG. 1 is shown containing a radiation detector system (an example of a sensor system) 110 and a radiation source 130. Radiation source 130 is a source of gamma rays (gamma photons) numbered 131. Radiation detector system 110 is shown containing detector 111 and readout and processing portion 112.

Detector 111 represents a gamma detector, and may be made of a suitable gamma detector material, such as for example, Cadmium Zinc Telluride (CZT). As is well known in the relevant arts, CZT is a semiconductor that converts gamma photons into electrons and holes. Although not shown, a potential difference is applied across surfaces 111-C (cathode) and 111-A (anode) of detector 111 which results in accumulation of electrons on 111-A (anode) electrodes. Anode surface 111-A is typically made of several pixelated areas (anode pixels), and each anode pixel is connected to charge sensitive preamplifiers/integrators which output electric current that has a magnitude that is proportional to the intensity of gamma photons incident on a corresponding portion of the opposite surface 111-C and which may penetrate into detector 111 to a corresponding depth depending on the intensity.

Readout and processing portion 112 is designed to contain one or more readout circuitry and processing circuitry. Readout circuitry within portion 112 receives and converts the electrical charges from each anode pixel to corresponding voltage levels, may optionally perform signal conditioning (e.g., amplification and filtering), and stores and/or forwards the voltage levels to processing circuitry in portion 112. Processing circuitry may contain processing elements such as analog-to-digital converters (ADC), processing blocks, power supplies, etc., and operates to extract information of interest from the voltage levels. Portion 112 outputs the result of processing on path 119. Thus, radiation detector system 110 operates to detect and process the effect (in the form of electric current) of gamma rays incident on detector 111.

As an example, the blocks of FIG. 1 may represent, or be parts of, a SPECT (single-photon emission computed tomography) system used for nuclear imaging and diagnostics. In such a context, radiation source 130 may represent a human patient injected with a gamma-ray emitting radioisotope. Readout and processing portion 112 may together operate to generate 3D images (information of interest noted above) of the internals of the patient's body based on the gamma rays incident on detector 111, and provide the 3D images on path 119 for further processing or display, where they can be viewed and interpreted by a medical expert.

Detector 111 may be implemented to contain a large number of anode pixels at high density. The arrangement of readout and processing portion 112 according to several aspects of the present disclosure enable such high density, and is described next with respect to embodiments.

3. Enabling Higher Pixel Density

Figure 2A:
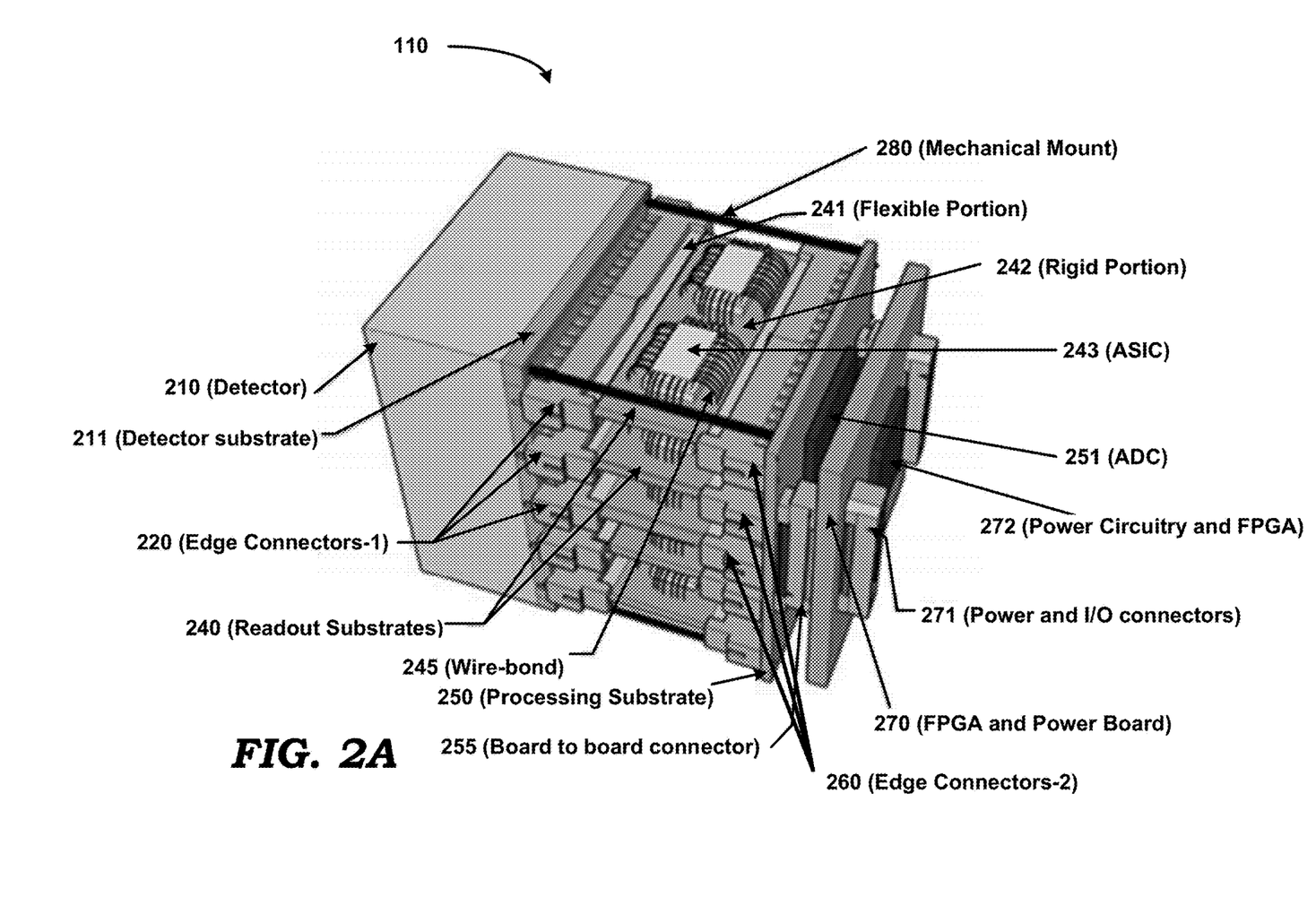
FIGS. 2A through 2F are diagrams depicting various views of a radiation detection system in an embodiment of the present disclosure.
Figure 2B:
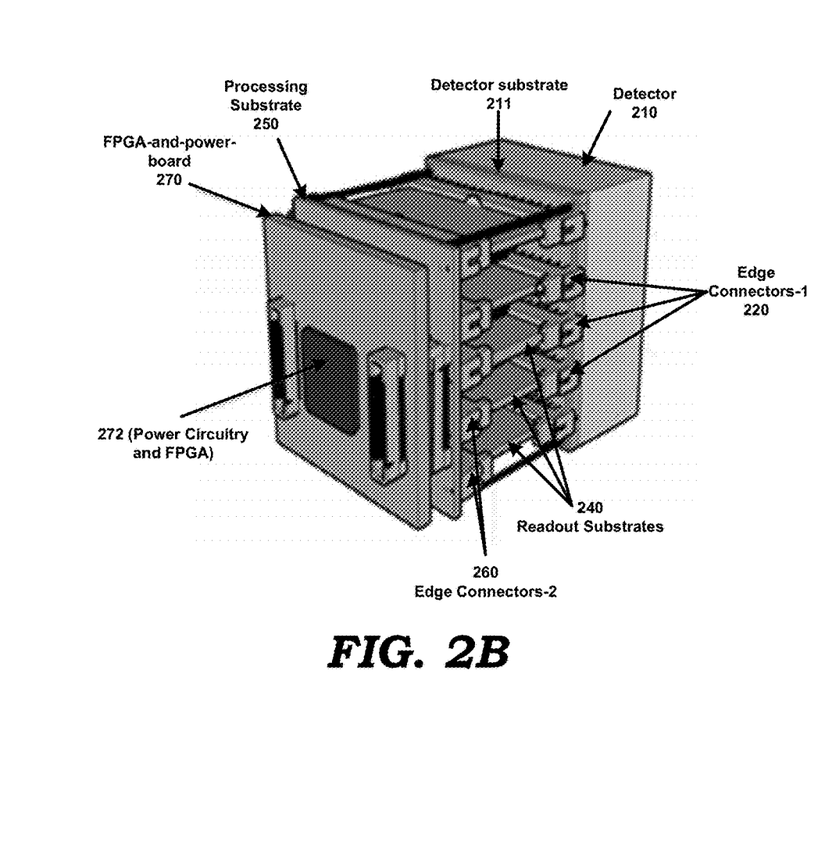
Figure 2C:
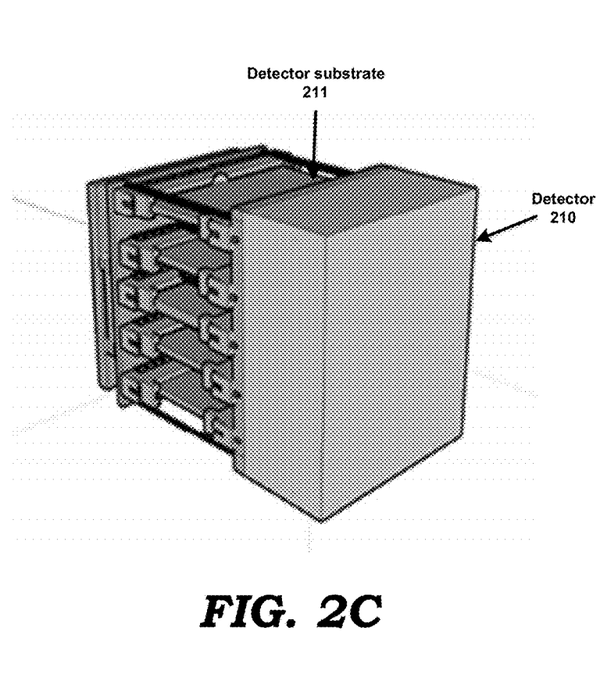
Figure 2D:
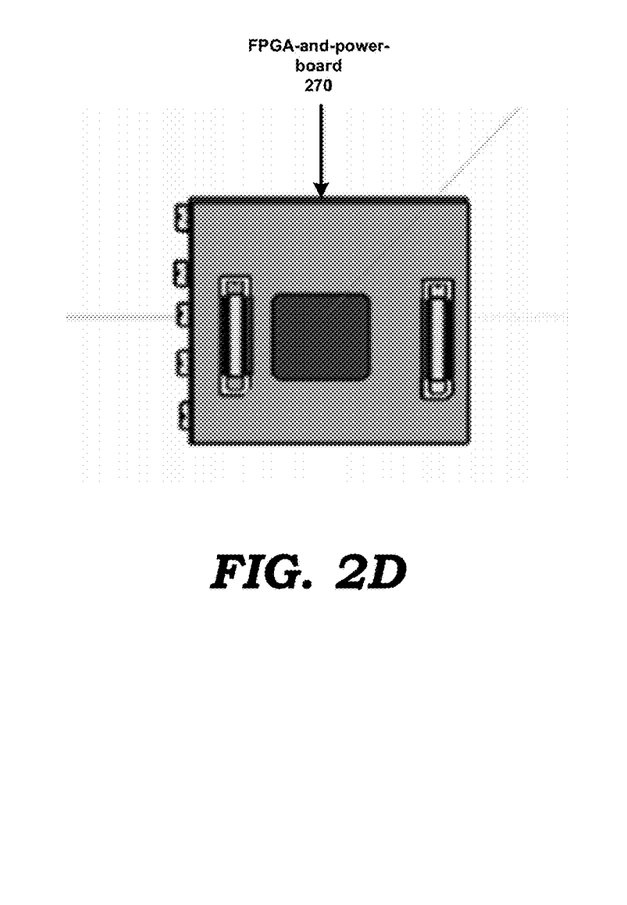
Figure 2E:
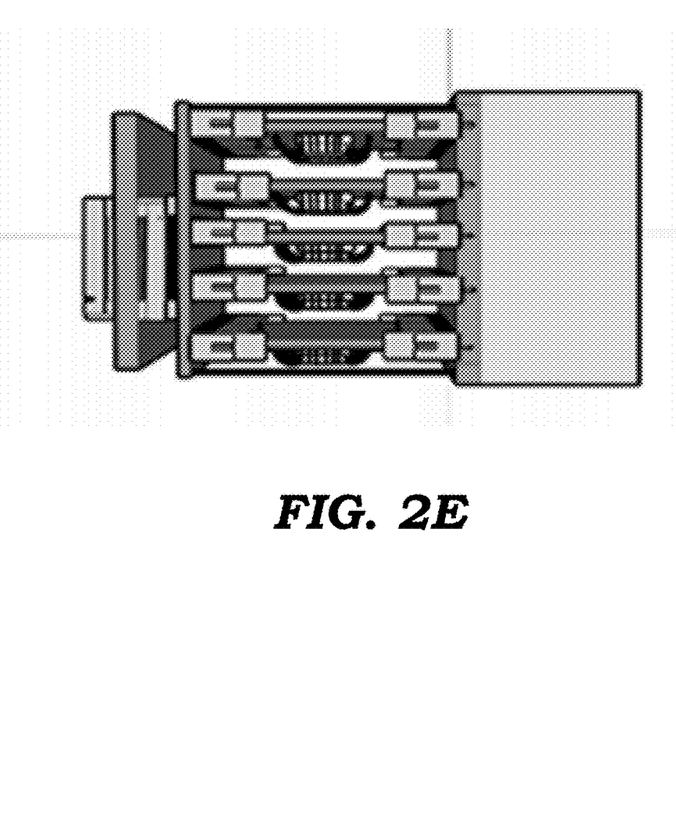
Figure 2F:
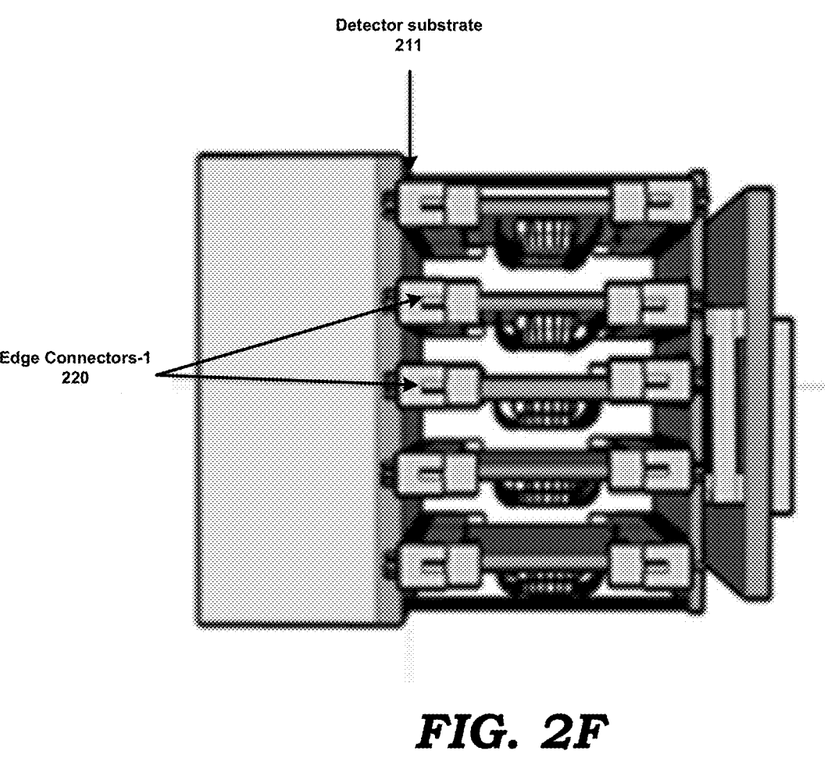

According to aspects of the present disclosure, readout and processing portion 112 is designed to enable high pixel density in the pixels (e.g., anode pixels) of detector 111. FIGS. 2A-2F are diagrams illustrating various views of the arrangement of components/blocks of readout and processing portion 112 of radiation detector system 110 of FIG. 1 in an embodiment of the present disclosure. In some of those Figures, detector 111 of FIG. 1 is shown as detector 210. Referring to FIG. 2A, the Figure shows detector 210, detector substrate 211, edge connectors-1 220, readout substrates 240, flexible portion 241, rigid portion 242, application specific integrated circuit (ASIC) 243, wire-bond 245, processing substrate 250, analog-to-digital-converter (ADC) 251, board-to-board connector 255, edge connectors-2 260, FPGA-and-power-board 270, power-and-I/O connectors 271 and mechanical mounts 280. The specific numbers of the various components noted above are shown in the Figures merely by way of illustration, and fewer or greater numbers of these can also be used.

As described in detail further below, according to an aspect of the present disclosure, readout substrates (containing readout circuitry) are stacked one above the other, with each readout substrate disposed perpendicular to the detector substrate (containing gamma detector). Further, processing substrate (containing processing elements to process the outputs of the readout circuitry) is also disposed perpendicular to each readout substrate and parallel to the detector substrate. Such a geometrical arrangement of the respective substrates enables detector 210 to be implemented to have a large number of anode pixels at very high density.

As used herein, the term 'substrate' refers to a solid substance or platform, currently available or which may be available in the near future, on which electronic circuitry may be mounted, and on which electrical connections via conductive traces may be made between nodes of the electronic circuitry and/or nodes of the electronic circuitry and external circuitry (for example using connectors or direct 90-degree solder joints). Thus, the term 'substrate' includes printed circuit boards (PCB) made of any suitable material such as, but not limited to, fiber glass epoxy, paper circuit boards, bio-composite boards, organic substrates, ceramic substrates, etc. Also, the term 'perpendicular' as used herein refers to right angles (ninety degrees) as well as angles deviating from ninety degrees by a small range lying within, for example, +/−3 degrees.

Continuing with reference to FIG. 2A, detector 210 may employ Cadmium Zinc Telluride (CZT, although other materials can also be used) as the gamma detector material, and is mounted on detector substrate 211. The surface (anode surface) of detector 210 that rests on detector substrate 211 is pixelated to contain anode pixels arranged in multiple rows, thus forming an array of pixels. The surface opposite to the anode surface is the cathode surface/terminal. Although not indicated in FIGS. 2A-2F, a potential difference is applied between the two opposite surfaces noted above that causes each anode pixel to accumulate electric charge as an output in response to gamma photons impinging at a corresponding portion (substantially opposite) on the cathode surface. The magnitude of accumulated charge at each of the pixel is proportional to the intensity of gamma photons impinging on the corresponding portion of the cathode surface, and therefore the depth to which the gamma photons penetrate the detector 210. The currents are available at corresponding electrical taps (e.g., signal pads or plated-through holes/PTH) arranged as multiple rows over the area of detector substrate 211. Edge connectors-1 (220, of which five are shown in FIG. 2A, but only the top three labeled as 220) connect each row of taps on detector substrate 211 to respective readout substrate and circuitry thereon.

Readout substrates 240 (five are shown in FIG. 2A of which only the top two are labeled as 240) are disposed perpendicular to detector substrate 211 and stacked one above the other. Readout circuitry in the form of ASICS 243 is mounted on each readout substrate 240. Connections to input terminals/nodes of ASICs 243 on each readout substrate 240 may be provided in the form of electrical taps (signal pads or PTH) arranged in the form of a row along the side of the readout substrate close to or aligned with the corresponding edge connector 220. Thus, ASICs on each readout substrate 240 receive the corresponding electrical currents from corresponding anode pixels, and convert the current to a voltage. The voltages generated by ASICs 243 on each readout substrate are available on corresponding electrical taps (signal pads or PTH) in the form of a corresponding row at the opposite side of the readout substrate. The ASICs may also perform operations such as amplification and filtering in generating the voltages. In FIG. 2A, each row of such electrical taps is connected to a corresponding edge connector 260 (edge connectors-2, of which five are shown in FIG. 2A, but only the top three labeled as 260). Bonding wires 245 are used to connect terminals/nodes of the ASICs to signal and power tracks on each readout substrate.

Each readout substrate 240 is made of a rigid portion 242 (on which the ASICs are mounted) and flexible portions 241 on either side of the rigid portion 242 that connect the rigid portion 242 to the corresponding pair of edge connectors 220 and 260. Each edge connector 220 and 260 is very dense in terms of number of connections per unit area. As an example, the combination of the flexible portion and the corresponding edge connector may be implemented in the form of a flexible flat fable (FFC) connector of around 0.25 mm pitch. In such an implementation, the spacing between anode pixels on detector 210 can be about 0.5 mm.

Processing substrate 250 is disposed perpendicular to each of readout substrates 240 and parallel to detector substrate 211. In the embodiment, processing substrate 250 contains one or more analog-to-digital converters (ADCs) mounted thereon. Electrical connections to terminals/nodes of the ADCs are provided in the form of electrical taps (signal pads or PTH) arranged as rows across the area of processing substrate 250. Voltages available at each of edge connectors 260 are provided to the ADCs as inputs via the electrical taps. The ADCs convert the respective voltages to corresponding digital codes at the ADCs' sampling rate. The single signal obtained at the cathode surface of detector 210 is also made available to the ADCs via one of the ASICs.

Processing substrate is connected to the FPGA and power board (270) via board-to-board connector 255. Board 270 represents a substrate with power supply circuitry, FPGAs (Field Programmable Gate Arrays) and communication circuitry (wireless and/or wired) (together denoted by number 272) mounted on the substrate. The power supply circuitry contains voltage regulators to generate power supplies for use by circuitry on processing substrate 250, readout substrates 240 and detector substrate 211. The FPGAs receive the digital codes generated by the ADCs on the processing substrate as well as additional information such as X-Y coordinates of location of the corresponding pixels on the detector. The FPGAs send the received data to communication circuitry that transmit the data via wireless path and/or wired path (via power-and-I/O connectors 271) to a smartphone or a personal computer for reconstruction of the radiation image.

Although the processing substrate 250 has been described above as having only ADCs, in alternative embodiments, processing substrate 250 includes other circuits/ICs such as processors for reconstruction of the radiation image. Mechanical mounts (280) are rods (of which there are four, although only one is shown labeled) that connect detector substrate 211 and processing substrate 250 and give rigidity to the radiation detector system. It is noted here that although the geometrical layout of electrical taps on the various substrates is described above as being organized in the form of one or more rows, such a layout is not necessary, and other layout patterns can instead be employed.

FIGS. 2B-2F show other views of the radiation detector system 110 of FIG. 2A.

The description is continued with respect to another embodiment of radiation detector system 110.

4. Right-Angled Solder Joints by Solder Reflow

In another embodiment, the design and structure and geometrical orientations of the parts of a radiation detector system is substantially the same as that shown in FIGS. 2A-2F, with the exception that the electrical connections between readout substrates and detector substrate (and optionally between readout substrates and processing substrate) are achieved by using an alternative approach of the standard reflow process for substrate assembly. The readout substrates, detector substrate and processing substrate may be slightly modified with respect to the respective electrical taps noted above. Since space-consuming connectors are note used for the electrical connections note above, the technique allows for even greater density of pixelation on the detector substrate than the embodiment described above in which connectors are used.

To distinguish from the embodiment illustrated in FIGS. 2A-2F, readout substrates, processing substrate and detector substrate in the embodiment described below are referred to using numerals 340, 350 and 360 respectively.

In the embodiment, electrical connections between detector substrate 360 and readout substrates 340 are not provided using connectors. Instead, the electrical connections are made by means of right-angled-solder-joints (without the use of any space-consuming connectors such as 220 of FIG. 2A), with all the readout substrates and detector substrate (and optionally with processing substrate also) in place, through a solder reflow process. The reflow process allows for solder reflow to occur with sufficient tolerance for self-aligning of the readout substrates 340. The electrical connections between readout substrates 340 and processing substrate 350 may be made using the same technique, or alternatively using connectors such as 260 of FIG. 2A. It is assumed in the description below that electrical connections between readout substrates 340 and processing substrate 350 are also made using the solder reflow technique.

As is well known in the relevant arts, reflow soldering is a technique used in assembly of electronics components (discrete and integrated circuits) and making electrical interconnections between nodes/terminals of the components on printed circuit boards (PCBs) or substrates in general. Solder paste (a mixture of powdered solder and flux) is first applied to the substrates on areas that need soldering to make temporary electrical connections between component leads/nodes and the substrates and/or connectors via pads or plated-through holes. The substrates have solder mask layers on them to electrically expose only the areas/islands that have signal pads or PTH that need soldering, as is well known in the relevant arts. The substrates are then positioned with respect to each other as desired, and electronic components are mounted on the respective substrates (typically with pick-and-place machines). The entire assembly is then heated until the solder paste melts and 'reflows' to make the desired electrical connections. The entire assembly may then be cooled until the electrical connections harden, thereby creating the desired permanent electrical connections between the component leads/nodes/pads and the substrates and/or connectors. The heating may be accomplished by passing the assembly through a reflow oven, under an infrared heat source, or (unconventionally) by soldering individual joints with a de-soldering hot air pencil.

A right-angled-solder-joint refers to an electrical connection between a pair of traces each on a pair of different substrates that are disposed at 90 degrees angle with respect to each other. The manner in which reflow soldering is used to make right-angled-solder-joints without the use of connectors (such as 220 or 260 of FIG. 2A) between readout substrates 340 and each of detector substrate 360 and processing substrate 350 is described next.

Figure 3:
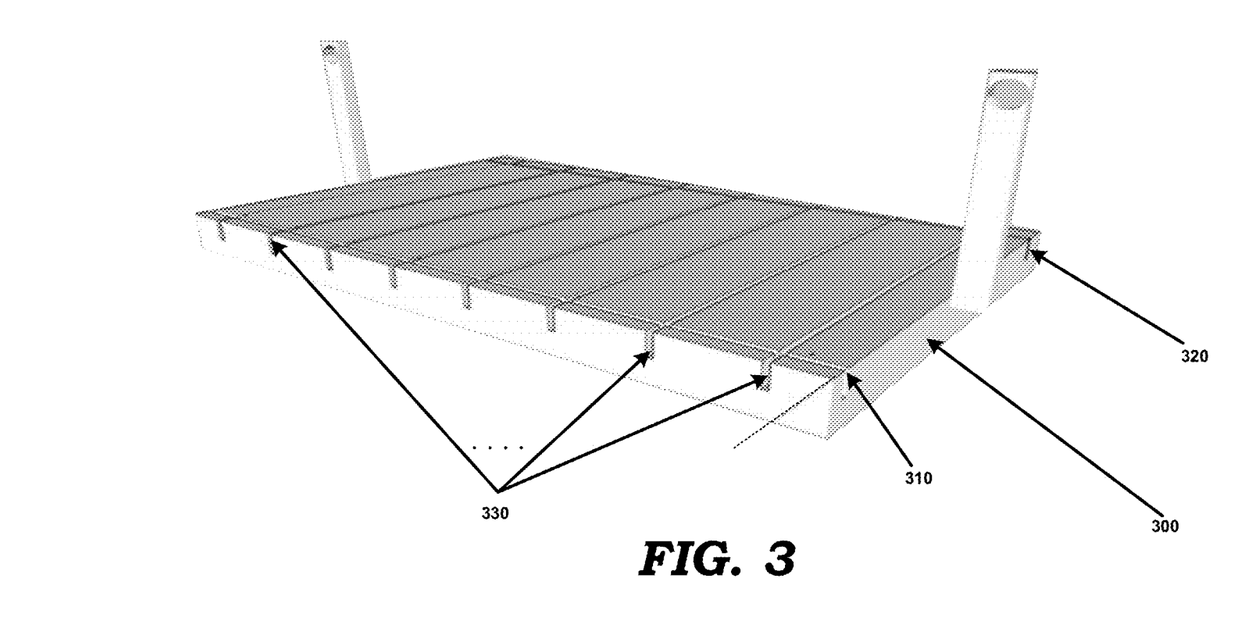
FIG. 3 is a diagram depicting a jig that is used for assembly of and making interconnections in a radiation detection system in another embodiment of the present disclosure.
Figure 4:
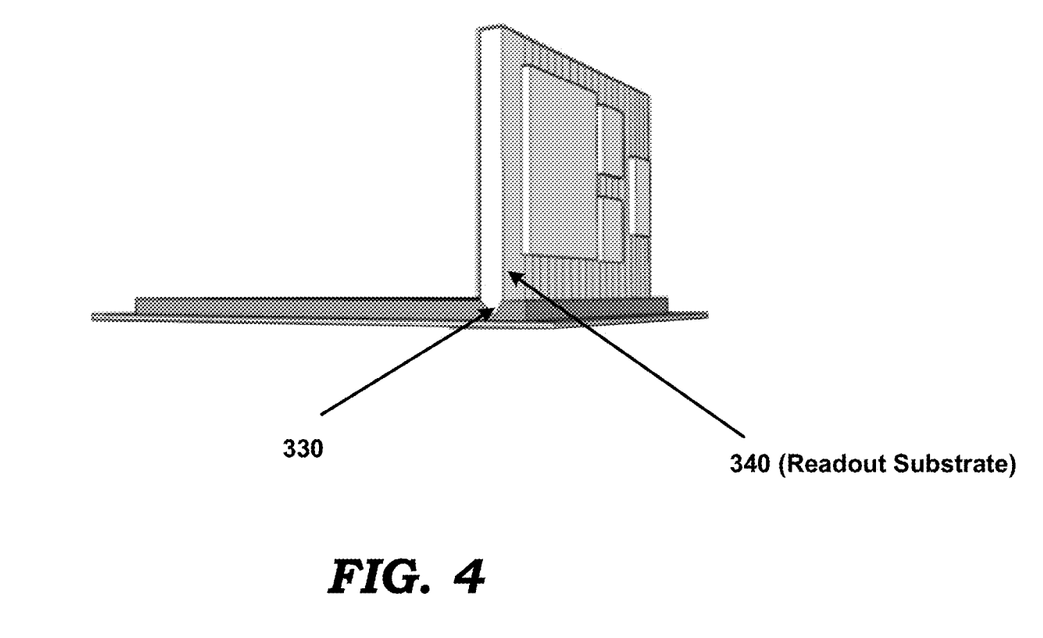
FIG. 4 is a diagram showing a single readout substrate positioned in a slot of a jig used for assembly of and making interconnections in a radiation detection system in an embodiment of the present disclosure.

FIG. 3 shows a part of a jig used in the solder reflow process for making the right-angled-solder-joints noted above. The jig has a base 300. Base 300 contains slots 310 and 320 parallel to each other and along one direction. Base 300 contains multiple parallel slots 330 along a direction orthogonal to that of slots 310 and 320. Readout substrates 240 are positioned in respective ones of slots 330. Detector substrate 360 and processing substrate 350 are positioned in slots 310 and 320 respectively. FIG. 4 shows one readout substrate 340 positioned on a slot 330.

Figure 5:
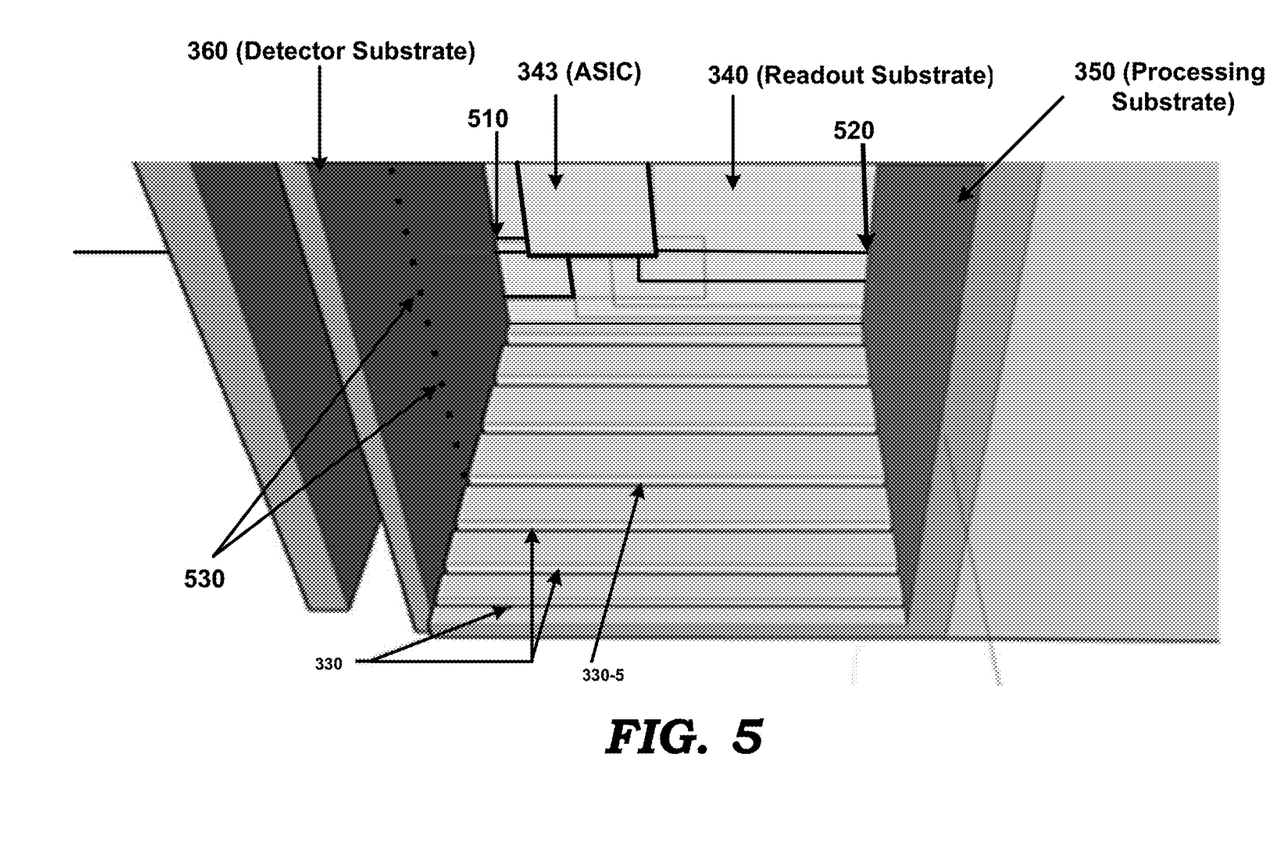
FIG. 5 is a diagram showing a jig with a detector substrate, a processing substrate and one readout substrate positioned in slots during the assembly and interconnection process of a radiation detection system in an embodiment of the present disclosure.

Each of readout substrates 340 is implemented to have electrical traces to/from respective ASICs mounted thereon to be connected to detector substrate 360 terminating on one edge (the edge touching detector substrate 360 when positioned in the respective slots of the jig). Similarly, each of readout substrates 340 is also implemented to have electrical traces to/from respective ASICs mounted thereon to be connected to processing substrate 350 terminating on the opposite edge (the edge touching processing substrate 350 when positioned in the respective slots of the jig). FIG. 5 illustrates such electrical traces. ASIC 343 on a readout substrate 340 is shown there. Electrical trace 510 from a terminal/node of ASIC 343 is shown terminating on the edge touching detector substrate 360. Electrical trace 520 from a terminal/node of ASIC 343 is shown terminating on the edge touching processing substrate 350.

Detector substrate 360 is designed to have electrical traces from anode pixels terminating on signal pads that would touch corresponding ends of electrical traces on the corresponding readout substrate 340 when assembled. As an example, a row of signal pads or PTH (electrical taps in general) 530 is shown in FIG. 5. Signal pads 530 would touch ends of electrical traces on a readout substrate positioned on slot 330-5. There would be other rows of signal pads/PTH (electrical taps) to allow electrical connection with other readout substrates. Processing substrate 350 would have similar signal pads and traces to connect with corresponding traces on corresponding readout substrates. Thus, each of detector substrate 360 and processing substrate 350 are designed to have signal pads/PTH (electrical taps) arranged as corresponding rows, although other geometrical layouts of the signal pads can also be used. It is noted again that although the geometrical layout of electrical taps on the various substrates is described above as being organized in the form of one or more rows, such a layout is not necessary, and other layout patterns can instead be employed.

With the substrates positioned in the slots of the jig, reflow soldering is performed to form right-angles-solder joints as noted above. The reflow of solder at each right-angled-solder-joint exerts mechanical forces on each of the corresponding readout substrates 340 so as to force the readout substrates 340 to be perpendicular to the detector substrate 360 (as well as processing substrate 350), thereby self-aligning the stacked readout substrates 340. The materials used for the jig are chosen to allow for no significant expansion or contraction due to thermal shock normally observed during the reflow process. Also, the materials used are thermally non-conductive. The heat generated during the solder reflow is conducted away from the assembly using thermal pads (not shown, but which can be suitably placed at various positions in the overall assembly), and active cooling such as liquid cooling or Peltier cooling. For additional cooling efficiency, air is blown laterally through the readout substrates 340.

Figure 6:
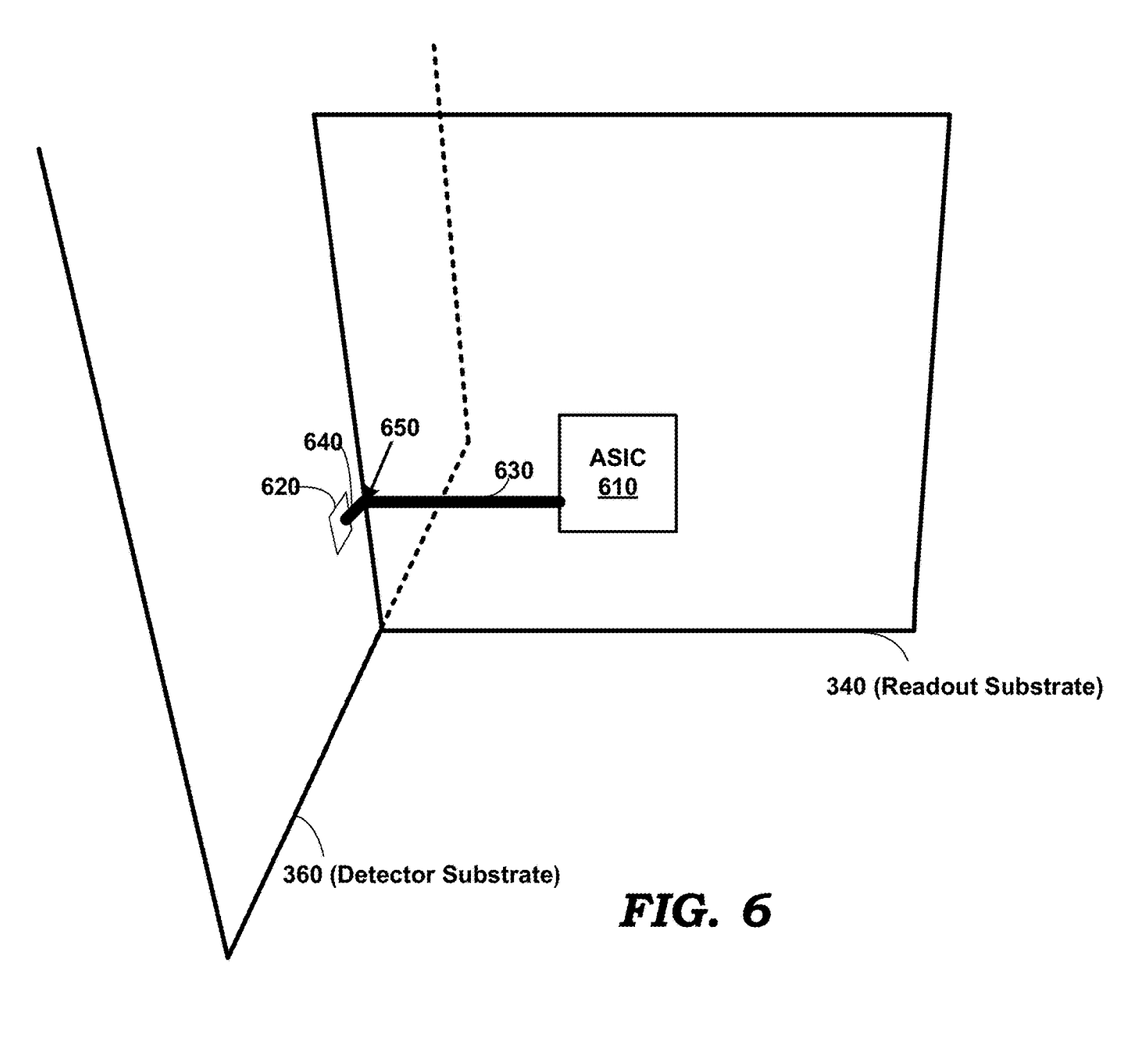
FIG. 6 is a diagram illustrating a right-angled-solder-joint formed according to several aspects of the present disclosure.

FIG. 6 illustrates a right-angled-solder-joint established as noted above. In the Figure, numeral 620 represents an anode pixel. Numeral 640 is an electrical trace from anode pixel 620 that is terminated at point 650. 630 is an electrical trace from a terminal of ASIC 610 that is terminated at the edge of readout substrate 340 at point 650. The solder reflow process creates a right-angled-solder-joint at point 650 between traces 640 and 630. After creation of all the right-angled-solder-joints, and/or completion of the electronic assembly process, the jig is removed from the assembled detector system.

5. Anode Pixel Array Layout

Figure 7A:
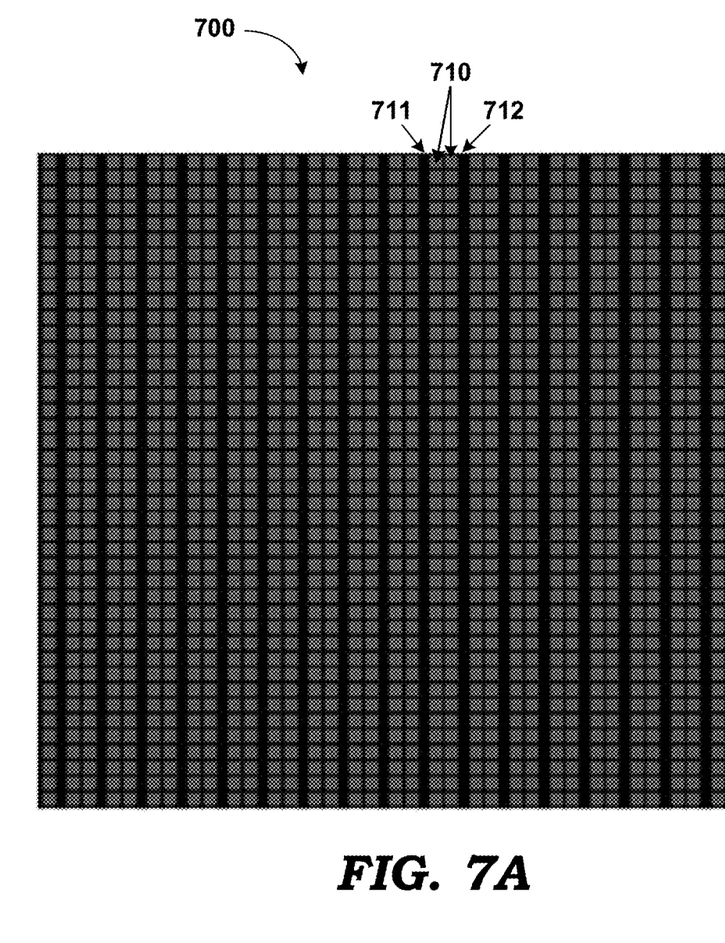
FIG. 7A is a diagram showing the layout of anode pixels on a detector, in an embodiment of the present disclosure.
Figure 7B:
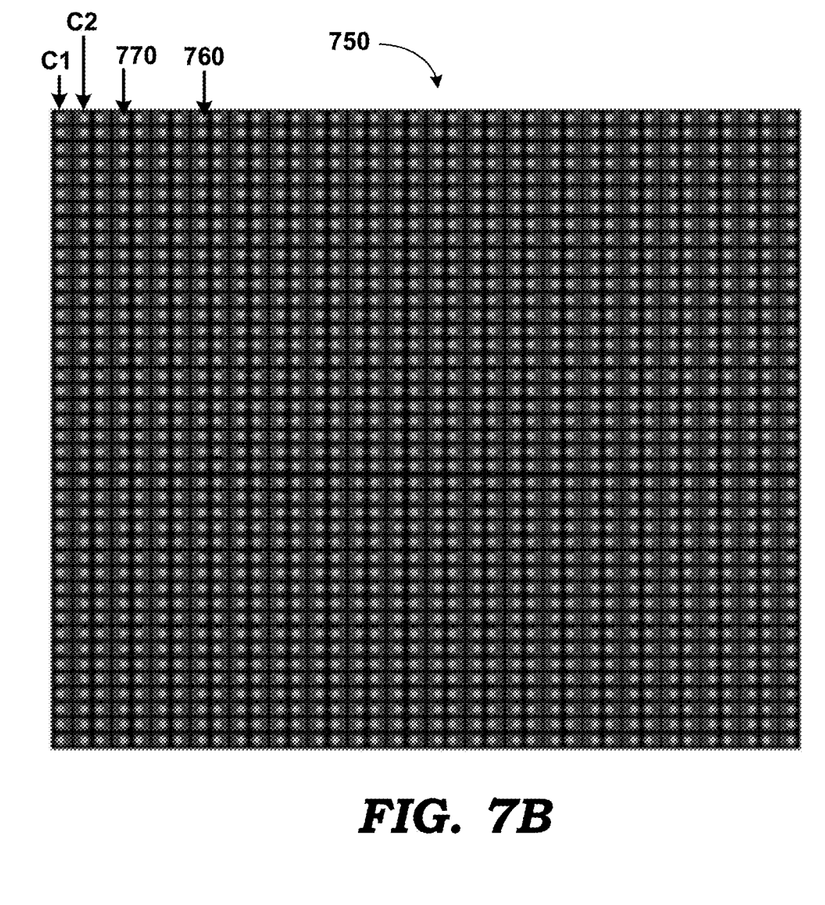
FIG. 7B is a diagram showing the layout of electrical taps on a detector substrate, in an embodiment of the present disclosure.

According to yet another aspect of the present disclosure, the array of anode pixels on detector substrate 360 is different from the conventional manner in which the array is laid out. FIG. 7A is a diagram illustrating the layout of anode pixels on the anode surface (e.g., 111-A in FIG. 1). Numeral 710 shows a pair of anode pixels in corresponding vertical columns of anode pixels. 711 and 712 represent gaps between the pair of vertical columns containing pixels 710 and a neighboring pair of columns of anode pixels to the left and to the right respectively. The gaps between pairs of adjacent columns align with the slots 330 of the jig shown in FIG. 3, and facilitate mounting of readout substrates 340 and the solder reflow process described above. FIG. 7B shows the reverse side 750 (side facing readout substrates 340) of detector substrate 360. 760 and 770 are example electrical taps (pads with via) on which the output of corresponding ones of a pair of anode pixels is available, and which are electrically connected to corresponding electrical traces on corresponding readout substrates through right-angled-solder-joints, as described above.

The effective electrical trace length between an anode pixel and the input (e.g., pre-amplifier input) of the corresponding ASIC is kept to a minimum and is comparable or smaller than the traditional horizontally mounted ASIC- Detector combination of the prior art. This is achieved through in pads as opposed to dog-bone vias, ultimately creating low inductance traces. In addition to routing lengths parallel runs of a pair of electrical traces from a corresponding pair of anode pixels are kept to a minimum to minimize cross-talk.

In an embodiment of the present disclosure, the detector substrate 360 has an area of 990 mils by 990 mils, and is fabricated to have two layers. Each layer (as shown in FIGS. 7A and 7B) has 1824 connections with through-holes (vias). The via position at the top layer exactly matches with the via at the bottom layer. The vias are capped and plated with conductive epoxy fill. The pads on the top layer (as shown in 700) are square in shape of size 16 mils by 16 mils, with 4 mils (1 mil=0.001 inch) space vertically between pairs of pads, with a total of 48 pads in a vertical direction. The pads on the top layer have 14 mils (as shown in 712) and 4 mils alternate spacing horizontally, with 38 pads totally in a horizontal direction. Thus, the pads on the top layer make up a 48×38 matrix/array. The pads at bottom (as shown in 750) are rectangular, with length same (16 mils) as that of a pad on top layer, but with a width of 19.5 mils, thus decreasing the space between pads horizontally. For example, in FIG. 7B, pads of column 1 (indicated as C1) are 3.5 mils wider to right while in the pads of column 2 (indicated as C2), the pads are wider to the left, and the same pattern follows.

In an embodiment of the present disclosure, there are 96 connections between each readout substrate and the detector substrate. There are a total of 19 readout substrates in a 2.4 cm by 2.4 cm area, resulting in a total of 1824 connections/pixels with 640 μm by 500 μm anode pixel size and 100 μm gap. This is a significant improvement over the current state-of-the-art, if not an order of magnitude. Such an advantage may be obtained while maintaining a fill factor (ratio of gamma ray-sensitive area of a pixel to total pixel area in the detector) of close to 100% with an ability to abut detectors to create large-area 2-dimensional arrays without any dead space.

6. Conclusion

References throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

While in the illustrations of FIGS. 2A-2F and 5, although terminals/nodes are shown with direct connections to (i.e., "connected to") various other terminals, it should be appreciated that additional components (as suited for the specific environment) may also be present in the path, and accordingly the connections may be viewed as being "electrically coupled" to the same connected terminals.

While various embodiments of the present disclosure have been described above, it should be understood that they have been presented by way of example only, and not limitation. Thus, the breadth and scope of the present disclosure should not be limited by any of the above-described embodiments, but should be defined only in accordance with the following claims and their equivalents.

What is claimed is:

1. A sensor system for generating a plurality of digital values representing gamma photons, said sensor system comprising:

a detector substrate and a detector mounted thereon, said detector to generate a plurality of detector output signals upon incidence of said gamma photons on said detector, said detector output signals being provided in the form of corresponding currents;

a plurality of readout substrates, each of said plurality of readout substrates disposed perpendicular to said detector substrate and having corresponding readout circuitry, wherein each readout circuitry converts a corresponding current to a voltage signal;

a processing substrate disposed perpendicular to each of said plurality of readout substrates and also parallel to said detector substrate, said processing substrate having a first surface and a second surface on either side of said processing substrate, said first surface to face said plurality of readout substrates; and one or more analog to digital converters (ADCs) mounted on said second surface of said processing substrate, wherein said processing substrate comprises a plurality of electrical taps on which said plurality of readout circuits are designed to terminate and provide said voltage signals, wherein each ADC is designed to receive a corresponding voltage signal from a corresponding electrical tap on said processing substrate and convert the voltage signal to a corresponding digital value of said plurality of digital values.

2. The sensor system of claim 1, wherein said detector output signals are terminated on corresponding taps of a first set of electrical taps on said detector substrate, wherein the readout circuitry on a corresponding readout substrate receives corresponding currents from taps of a second set of electrical taps disposed along a first edge of said corresponding readout substrate, wherein electrical connections between corresponding taps of said first set of electrical taps and said second set of electrical taps are made via one of a first type of electrical connection and a second type of electrical connection, wherein the readout circuitry on said corresponding readout substrate provides corresponding voltage signals on corresponding taps of a third set of electrical taps disposed along a second edge of the readout substrate, wherein said plurality of electrical taps of said processing substrate represent a fourth set of electrical taps, wherein electrical connections between corresponding taps in said fourth set of electrical taps and said third set of electrical taps are also made via one of said first type of electrical connection and said second type of electrical connection.

3. The sensor system of claim 2, wherein said first set of electrical taps are disposed in the form of rows on said detector substrate, wherein each of said second set of electrical taps and said third set of electrical taps are disposed in the form of corresponding rows, and wherein said fourth set of electrical taps are disposed in the form of rows on said processing substrate.

4. The sensor system of claim 3, wherein each of said first set of electrical taps, said second set of electrical taps, said third set of electrical taps and said fourth set of electrical taps are plated-through-holes (PTH).

5. The sensor system of claim 3, wherein some of the electrical taps in said first set of electrical taps, said second set of electrical taps, said third set of electrical taps and said fourth set of electrical taps are plated-through-holes (PTH), and the other ones of the electrical taps are surface mount pads.

6. The sensor system of claim 4, wherein said sensor system is a radiation detector system, wherein said detector is a gamma detector comprising Cadmium Zinc Telluride (CZT) material to detect said gamma photons, wherein said detector comprises a first surface forming a cathode terminal to receive said gamma photons, and a second surface parallel to said first surface and pixelated into a plurality of anode pixels arranged as multiple rows on said second surface, each of said anode pixels generating a corresponding detector output signal as a current proportional to the intensity of gamma photons incident on a corresponding portion of said cathode terminal, wherein all of said corresponding detector output signals together represent said plurality of detector output signals, said detector being mounted on said detector substrate with said second surface facing said detector substrate, wherein detector output signals from each row of said multiple rows of said anode pixels are terminated on a corresponding row of said first set of electrical taps.

7. The sensor system of claim 6, wherein said corresponding readout circuitry comprises application specific integrated circuits (ASICs) to convert received currents to corresponding voltages.

8. The sensor system of claim 7, further comprising a power-and-input-output (P-I/O) substrate having processing units and power supply units, said power supply units to provide power supplies to said ASICs, said ADCs and said processing units, wherein said processing units are designed to process said plurality of digital values to obtain information of interest from said plurality of detector output signals.

9. The sensor system of claim 7, wherein each of said plurality of readout substrates comprises a combination of a rigid portion and a flexible portion, wherein said ASICs are mounted on said rigid portion, and wherein said flexible portion is between said rigid portion and said first edge.

10. The sensor system of claim 9, wherein said first type of electrical connection is provided by right-angled solder joints using a solder-reflow process.

11. The sensor system of claim 10, wherein said second type of electrical connection is provided by edge connectors.

12. The sensor system of claim 11, wherein said first set of electrical taps are plated-through-holes (PTH), wherein said second set of electrical taps are signal pads at said first edge.

13. The sensor system of claim 12, wherein the anode pixels in each row of said multiple rows are organized to provide spaces between subsets of anode pixels in said each row to facilitate making of said first type of electrical connection.

* * * * *